United States Patent
Schumacher (10) Patent No.: US 10,359,415 B2
(45) Date of Patent: Jul. 23, 2019

(54) SINGLE-USE BIOREACTOR SENSOR ARCHITECTURE

(71) Applicant: Rosemount Inc., Chanhassen, MN (US)

(72) Inventor: Mark S. Schumacher, Minneapolis, MN (US)

(73) Assignee: Rosemount Inc., Shakopee, MN (US)

( * ) Notice: Subject to any disclaimer, the term of this patent is extended or adjusted under 35 U.S.C. 154(b) by 182 days.

(21) Appl. No.: 14/502,502

(22) Filed: Sep. 30, 2014

(65) Prior Publication Data
US 2015/0316528 A1 Nov. 5, 2015

Related U.S. Application Data (60) Provisional application No. 62/029,199, filed on Jul. 25, 2014, provisional application No. 61/987,726, filed on May 2, 2014.

(51) Int. Cl.
| | |
|---|---|
| *G01N 33/487* | (2006.01) |
| *G01N 33/483* | (2006.01) |
| *G01N 33/18* | (2006.01) |
| *C12M 1/00* | (2006.01) |

(52) U.S. Cl.
CPC ....... *G01N 33/487* (2013.01); *G01N 33/1806* (2013.01); *G01N 33/4833* (2013.01); *C12M 23/14* (2013.01); *C12M 23/28* (2013.01); *Y10T 29/49004* (2015.01)

(58) Field of Classification Search
CPC ....... G01L 15/00; C12M 23/28; C12M 23/14; G01N 33/487
See application file for complete search history.

(56) References Cited

U.S. PATENT DOCUMENTS

| | | | | |
|---|---|---|---|---|
| 5,460,049 | A | * 10/1995 | Kirsch | G01L 9/065 73/152.52 |
| 7,467,555 | B2 | * 12/2008 | Schulte | G01F 1/34 73/736 |
| 7,924,017 | B2 | 4/2011 | Ammann et al. | |
| 8,123,397 | B2 | 2/2012 | Baumfalk et al. | |
| 8,252,582 | B2 | 8/2012 | Baumfalk et al. | |
| 8,640,560 | B2 | 2/2014 | Burke | |

(Continued)

FOREIGN PATENT DOCUMENTS

| | | |
|---|---|---|
| JP | 2009-519440 A | 5/2009 |
| WO | 2009/146323 A | 12/2009 |
| WO | WO 2013-162394 A1 | 10/2013 |

OTHER PUBLICATIONS

International Search Report and Written Opinion for International Patent Application No. PCT/US2015/028192, dated Jul. 27. 2015, date of filing: Apr. 29, 2015, 18 pages.

(Continued)

*Primary Examiner* — Jonathan M Hurst
(74) *Attorney, Agent, or Firm* — Christopher R. Christenson; Kelly, Holt & Christenson PLLC (57) ABSTRACT

A sensor assembly includes a first sensor and a second sensor. An enclosure is operably coupled to each of the first and second sensors and contains memory that stores compensation data for each of the first and second sensors. A connector is operably coupled to the first and second sensors. A bioreaction sensing assembly as well as a method of manufacturing the bioreaction sensing assembly is also provided.

17 Claims, 5 Drawing Sheets

(56) References Cited

U.S. PATENT DOCUMENTS

| | | | |
|---|---|---|---|
| 9,267,100 B2 | 2/2016 | Edwards | |
| 2004/0027912 A1 | 2/2004 | Bibbo et al. | |
| 2005/0163667 A1 | 7/2005 | Krause | |
| 2007/0185680 A1 | 8/2007 | Kambe et al. | |
| 2008/0274541 A1* | 11/2008 | Selker | B01F 3/04248 435/289.1 |
| 2010/0017159 A1* | 1/2010 | Burke | A61L 2/081 702/81 |
| 2010/0302008 A1 | 12/2010 | Engelstad et al. | |
| 2011/0187388 A1 | 8/2011 | Ossart | |
| 2011/0201100 A1* | 8/2011 | Proulx | B01F 5/106 435/288.7 |
| 2012/0016603 A1 | 1/2012 | Martin et al. | |
| 2012/0240686 A1 | 9/2012 | Blomberg et al. | |
| 2012/0242993 A1 | 9/2012 | Schick et al. | |
| 2012/0244609 A1 | 9/2012 | Edwards | |
| 2012/0290268 A1* | 11/2012 | Bey | G01D 11/245 702/189 |
| 2013/0055821 A1* | 3/2013 | Bentley | G01L 9/0054 73/721 |
| 2013/0145818 A1 | 6/2013 | Allgauer et al. | |

OTHER PUBLICATIONS

First Chinese Office Action for Chinese Patent Application No. 201510197804.X, dated Jan. 26, 2017, including English Translation, 21 pages.
Patent Examination Report No. 1 for Australian Patent Application No. 2015253275, dated Nov. 15, 2016, 4 pages.
International Preliminary Report on Patentability for International Patent Application No. PCT/US2015/028192, dated Nov. 17, 2016, date of filing: Apr. 29, 2015, 15 pages.
Communication Pursuant to Rules 1611(2) and 162 EPC for European Patent Application No. 15786477.8, dated Dec. 9, 2016, 2 pages.
Second Office Action for Chinese Patent Application No. 201510197804.X, dated Sep. 29, 2017, 13 pages including English translation.
Office Action for Japanese Patent Application No. 2016-565389, dated Sep. 19, 2017, 7 pages including English translation.
Third Office Action, dated May 4, 2018, for Chinese Patent Application No. 201510197804.X, 20 pages including English Translation.
Office Action, dated May 29, 2018, for Japanese Patent Application No. 2016-565389, 6 pages including English translation.
"A low-cost system for real time monitoring and assessment of potable water quality at consumer sites", 2013 IEEE Sensors, IEEE, Oct. 28, 2012, pp. 1-4.
Rejection Decision dated Dec. 3, 2018, for Chinese Patent Application No. 201510198704.X, pp. 22 including English translation.

* cited by examiner

SINGLE-USE BIOREACTOR SENSOR ARCHITECTURE

CROSS-REFERENCE TO RELATED APPLICATIONS

The present application is based on and claims the benefit of U.S. Provisional Patent Application Ser. Nos. 62/029,199 filed Jul. 25, 2014 and 61/987,726 filed May 2, 2014, the content of which applications is hereby incorporated by reference in their entireties.

BACKGROUND

Bioreactors are useful for generating and supporting biological reactions for any number of purposes. Biological reactions can be susceptible to changes in temperature and/or pressure. Moreover, as the biological reaction progresses, the reaction itself may change various parameters within the bioreaction vessel, such as dissolved oxygen content and/or pH. Accordingly, it may be important to monitor a number of variables of the biological reaction.

The life sciences industry is moving from large, capital-intensive facilities made of stainless steel with large clean-in-place (CIP) infrastructure to smaller facilities that use polymer bags or containers functioning as the bioreactors. The bioreactor bag is used once and then disposed. This single-use bioreactor technique significantly reduces the capital cost of the plant. For example, in existing facilities that use stainless steel CIP infrastructure, up to 90% of the cost of operating the facility may be due to the clean-in-place infrastructure, including very high end instrumentation designed to withstand a steam cleaning cycle. By moving to disposable, single-use, bioreactor bags, the CIP portion of the capital can be eliminated and the facility can be more flexible and much smaller, which, in turn, allows the production of smaller batches that are needed for more targeted drug therapies and other smaller-scale applications. Providing an instrumentation architecture that facilitates the use and adoption of disposable, single-use bioreaction techniques would be of significant benefit to the life sciences industry, as well as other industries and processes that generate such biological reactions.

SUMMARY

A sensor assembly includes a first sensor and a second sensor. An enclosure is operably coupled to each of the first and second sensors and contains memory that stores compensation data for each of the first and second sensors. A connector is operably coupled to the first and second sensors. A bioreaction sensing assembly as well as a method of manufacturing the bioreaction sensing assembly is also provided.

DETAILED DESCRIPTION OF ILLUSTRATIVE EMBODIMENTS

Figure 1:
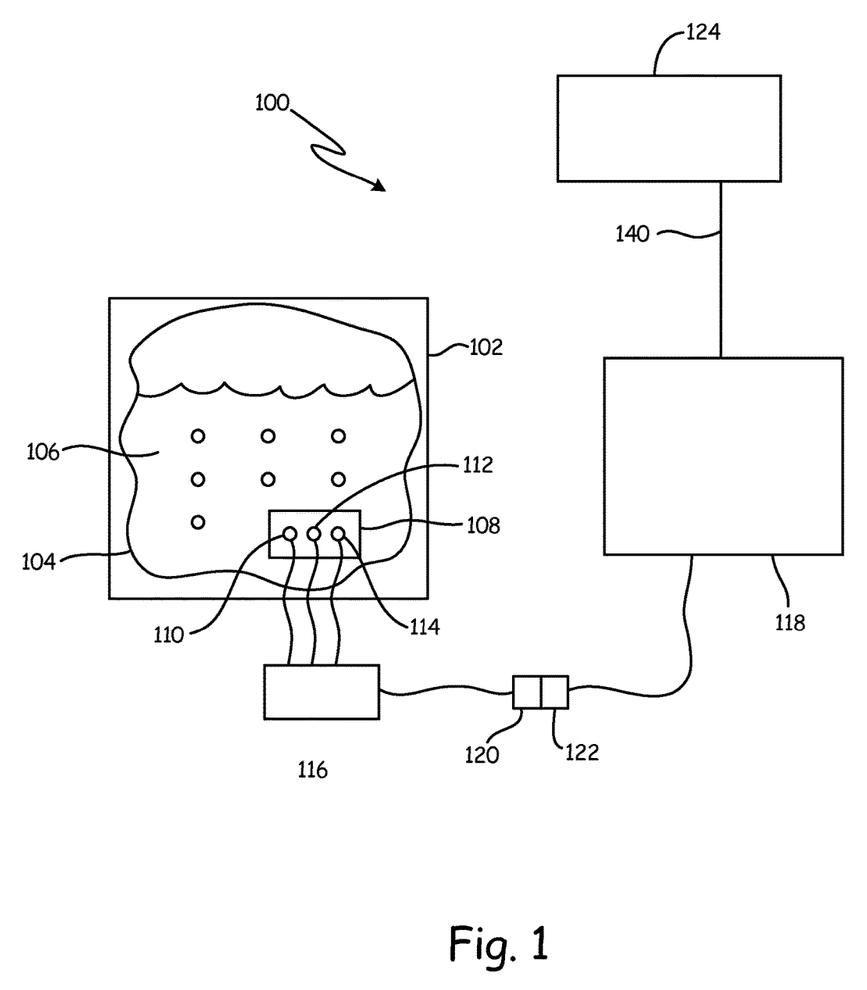
FIG. 1 is a diagrammatic view of a single-use bioreaction system in accordance with an embodiment of the present invention.

FIG. 1 is a diagrammatic view of a bioreaction sensing system in accordance with an embodiment of the present invention. System 100 includes a structural holding vessel 102 that contains a poly bag 104 supporting a biological reaction occurring in sample 106. In the embodiment illustrated in FIG. 1, a process window 108 is provided that facilitates coupling individual sensors 110, 112 and 114 to the biological reaction. Sensors 110, 112 and 114 typically sense different variables of the biological sample. Such sensors can include temperature sensors, pressure sensors, dissolved oxygen sensors, carbon dioxide sensors, conductivity sensors, pH sensors, colorimetric sensors, or any other suitable sensors. Process window 108 facilitates coupling the various sensors to the biological specimen. For example, while maintaining a fluid tight window in the poly bag 104, a portion in window 108 maybe highly permeable to oxygen, which would facilitate the utilization of an oxygen sensor external to the bag. However, embodiments of the present invention also include simply disposing one or more of sensors 110, 112 and 114 within the bag itself and sealing the electrical connections of the sensors as they pass through the bag wall. Additionally, while the embodiment illustrated with respect to FIG. 1 shows three distinct sensors 110, 112, and 114, fewer sensors or more sensors may be used in accordance with embodiments of the present invention. Additionally, while the embodiment described thus far has been described with respect to different sensor types, it is also expressly contemplated that two sensors may be of a similar type but have a different operating characteristic or range. For example, a first pressure sensor may have a range of 0-100 PSI, while a second pressure sensor may only have a range between 5-10 PSI but may have very high accuracy and precision within the noted range.

By providing a relatively standardized location and size for process window 108, various configurations of multiple different sensor types can be provided. However, polymeric bags can be mass produced based on the standardized size and location of the process window. Thereafter, specialization of individual bioreactor bags and sensing assemblies can be provided by welding, sealing, or otherwise affixing a window 108 to a polymeric bag 104. Thus, economies of scale can allow the production of the polymeric bag to occur at high quantities thereby reducing the overall cost of the bag itself.

As illustrated in FIG. 1, each of sensors 110, 112, 114 is coupled to compliance box 116, which is then coupled to process variable transmitter 118 via connectors 120 and 122. The process variable transmitter is able to measure the analog signals of the various sensors 110, 112, 114, and compute related variables, such as temperature, pressure, pH, etc. based on the measured analog signals. Additionally, these computed variables can then be transmitted to control system 124 in any suitable manner, including process communication, such as that in accordance with the Highway Addressable Remote Transducer (HART®) protocol, or the FOUNDATION™ Fieldbus protocol, for example. As illustrated in FIG. 1, the array of sensors 110, 112, 114 is embedded or otherwise disposed within single-use bioreactor bag 104. Either prior to or after embedding the various sensors 110, 112, 114 in bag 104, the sensor array is subjected to a characterization process as part of the manufacture. This characterization process produces a data set that is used to compensate the individual sensors of the sensor array. This compensation allows the raw analog signals measured by process variable transmitter 118 to be accurately mapped or otherwise transformed to process variable outputs. For example, pH is known to be highly temperature dependent. The characterization process uses a temperature sensor to compensate the pH sensor. Compensation curve information or data are loaded into and stored locally within compliance box 116. The compensation curve information or data are unique to the individual sensors in the array.

In some embodiments, compliance box 116 may include an RFID device that may store any sensor-specific data. Such data includes not only compensation curve information and data, but additional data that may be required by the end user, or a regulatory agency, such as the Food and Drug Administration. Further information can include material of construction, manufacture date, serial number, operating range, signal type (such as resistance or voltage), et cetera.

In operation, when connector 120 is coupled to connector 122, compliance box 116 is able to communicate with process variable transmitter 118. Process variable transmitter 118 then reads the data stored within compliance box 116 and employs the compensation curve information or data to enhance the performance of the sensors in the array. Process variable transmitter 118 measures one or more raw sensor analog signals; applies a compensation function to the measured raw analog signal to obtain one or more compensated process variables; and conveys the compensated process variables to control system 124.

In some instances, it is required by the regulatory agency that an instrument calibration be performed at the end of a batch run in order to ensure that the instrument was operating within its operating range during the batch run. In the case of the sensor array illustrated with respect to FIG. 1, a "batch-check" buffer solution of known parameters can be loaded into bag 104, and the array's output can be checked against this known reference. Since the array and the "batch-check" solution will be disposed of, there is no need for any clean-in-place (CIP) capability. Further, since the reference instruments used to establish the "batch-check" solution parameters never contact the product, standard instrumentation can be used for this application.

When the bioreaction is complete, bag 104, as well as sensors 110, 112, and 114 and compliance box 116 can be disposed or otherwise discarded. Process variable transmitter 118 is retained and is used to interact with the next sensor array/bioreaction system.

Figure 2:
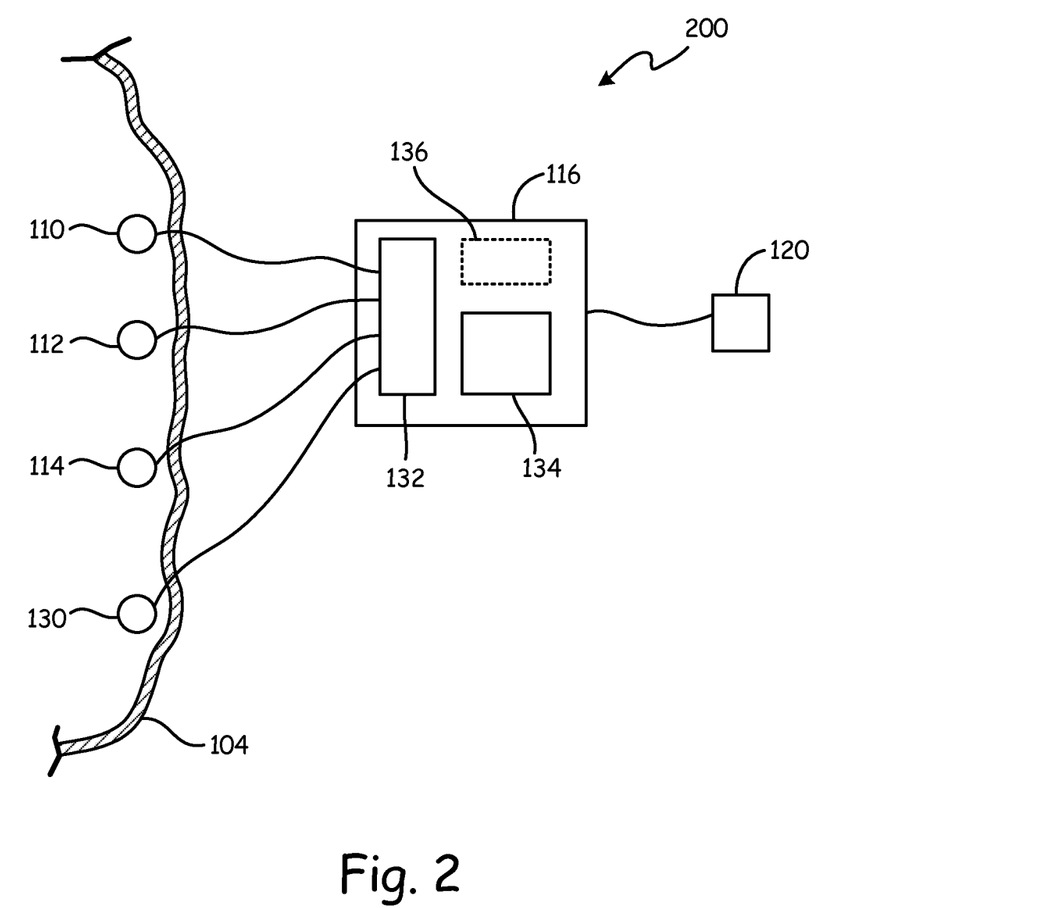
FIG. 2 is a diagrammatic view of a sensor assembly incorporated into a single-use bioreaction bag in accordance with an embodiment of the present invention.

FIG. 2 is a diagrammatic view of a sensor array assembly incorporated into a bioreaction bag in accordance with an embodiment of the present invention. Assembly 200 is similar to the assembly illustrated with respect to FIG. 1, and like components are numbered similarly. Specifically, a number of sensors 110, 112, 114, and 130 are disposed within bioreaction bag 104. However, unlike the arrangement illustrated with respect to FIG. 1, assembly 200 in FIG. 2 does not include a process window. Instead, sensors 110, 112, 114, and 130 are merely located within the interior of bioreaction bag 104. Each sensor 110, 112, 114 and 130 includes leads that pass through bag wall 104 and couple to compliance box 116. In one embodiment, each of sensors 110, 112, 114, and 130 couple to suitable signal conditioning circuitry 132 disposed within compliance box 116. Signal conditioning circuitry 132 includes one or more preamplifiers that boost or otherwise strengthen the analog signals of the various sensors 110, 112, 114, and 130. The provision of one or more preamplifiers within signal conditioning circuitry 132 is advantageous because the raw analog output of sensors such as pH, conductivity, dissolved oxygen and many others is a low level millivolt signal. A preamplifier is able to boost this signal so that it can be effectively measured by process variable transmitter 118. Additionally, it is expressly contemplated that the signal conditioning circuitry 132 can include several preamplifiers such that each sensor could be coupled to its own preamplifier. In one embodiment the preamplifier(s) is/are disposed relatively close to the sensors. However, given that the sensors are embedded in a bioreaction bag 104, the harsh sterilization process to which the sensors are subjected could damage the circuitry of the preamplifier. The bag/sensor/wire system is typically sterilized using a heat and/or a radiation process. The sensors can be designed to withstand the sterilization process. However, by moving the preamplifier circuitry into the compliance box, it is safely protected from the sterilization process and will not need to be designed to withstand such process.

Compliance box 116 includes local data storage 134 as well as a communication interface such that the data stored within data storage device 134 can be communicated through connector 120. However, embodiments of the present invention are contemplated wherein the communication of data from local storage 134 to process variable transmitter 118 is done wirelessly, in accordance with known RFID communication techniques.

Since the entire assembly illustrated with respect to FIG. 2 is essentially disposable, it is preferred that the various components thereof be relatively low-cost in order to reduce the overall operating costs. In one embodiment, data storage device 134 includes an RFID tag that is written or otherwise loaded with data during the manufacture and characterization of the sensor assembly. However, other low-cost memory infrastructures can be used, including flash memory.

Compliance box 116 may include one or more local sensors 136 that are disposed within compliance box 116 and that are able to sense environmental conditions proximate or within compliance box 116. One example of such a sensor is an absolute pressure sensor. When an absolute pressure sensor is used to compensate for changes in atmospheric pressure, it allows an absolute pressure sensor to be used within the bioreactor bag. The utilization of such dual absolute pressure sensors eliminates the need for a gauge vent tube leading from the bag sensor to the outside environment. Such a gauge vent tube is a potential source for contamination from the environment to the bag, and elimination of this vent tube is advantageous in many bioreaction contexts.

Figure 3:
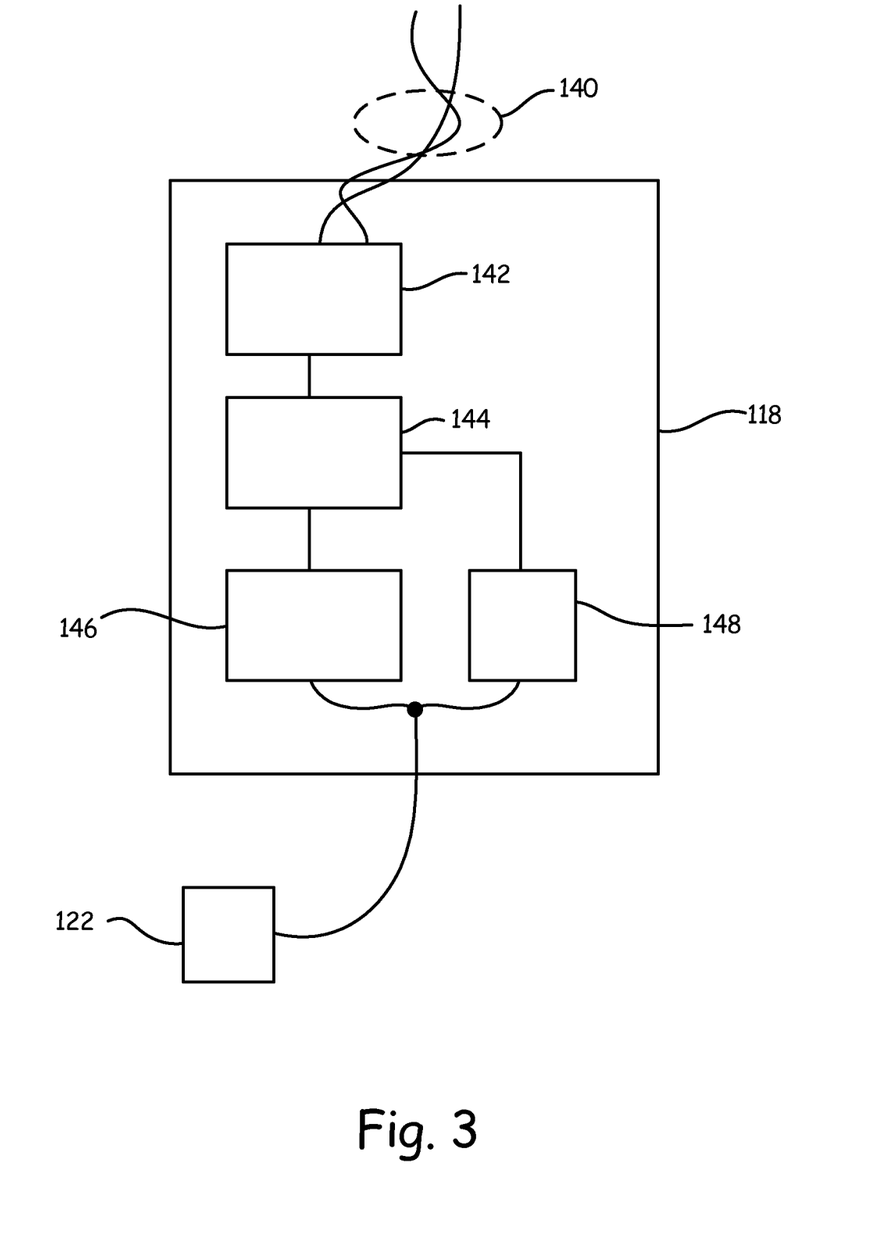
FIG. 3 is a diagrammatic view of a process variable transmitter couplable to a single-use bioreaction sensing system in accordance with an embodiment of the present invention.

FIG. 3 is a diagrammatic view of a process variable transmitter that is couplable to a sensor assembly in accordance with an embodiment of the present invention. Process variable transmitter 118 includes a process communication module 120 that is couplable to a process communication loop or segment 140 in order to allow the process variable transmitter 118 to communicate with control system 124, or any other suitable device. This communication is in accordance with process communication protocol such as the HART® or the Fieldbus protocol described above. Additionally, wireless process communication protocols, such as that in accordance with IEC62591 are also contemplated. Process communication module 142 is coupled to processor 144, which may be, in some embodiments, a microprocessor. Processor 144 is able to programmatically calculate one or more process variables based on measurements of the raw sensor values obtained from the sensor assembly. Processor 144 is coupled to measurement circuitry 146 which may include, for example, an analog-to-digital converter. Measurement circuitry 146 is operably coupled to one or more sensors of the sensor array through connector 122. Measurement circuitry 146 provides an indication of the raw, analog, signals provided by each of the individual sensors of the sensor array to processor 144. Processor 144 is also coupled to data storage device reader 148. Data storage device reader 148 is configured to interact with the data storage device 134 of compliance box 116 in order to read the data stored within data storage device 134. As set forth above, such data will include characterization/compensation curves or data with respect to each sensor of the sensor array. Additional data can include that desired to be stored by the end user, as well as any data required for traceability from a regulatory agency or other entity. As shown in FIG. 3, data storage device reader 148 may be coupled to compliance box 116 via connector 122. However, embodiments of the present invention can be practiced where the interaction between data storage device reader 148 and storage device 134 is wireless. An example of suitable technology for interacting with a sensor having local storage is provided in United States Patent Application Publication Number 2010/0302008 assigned to the Assignee of the present invention. However, the communication between data storage device reader 148 and data storage device 134 can also be in accordance with known low-level communication techniques, such as I²C, Controller Area Network (CAN) bus, or the serial peripheral interface (SPI). However, those skilled in the art will recognize that any suitable communication protocol or technique can be employed.

Figure 4:
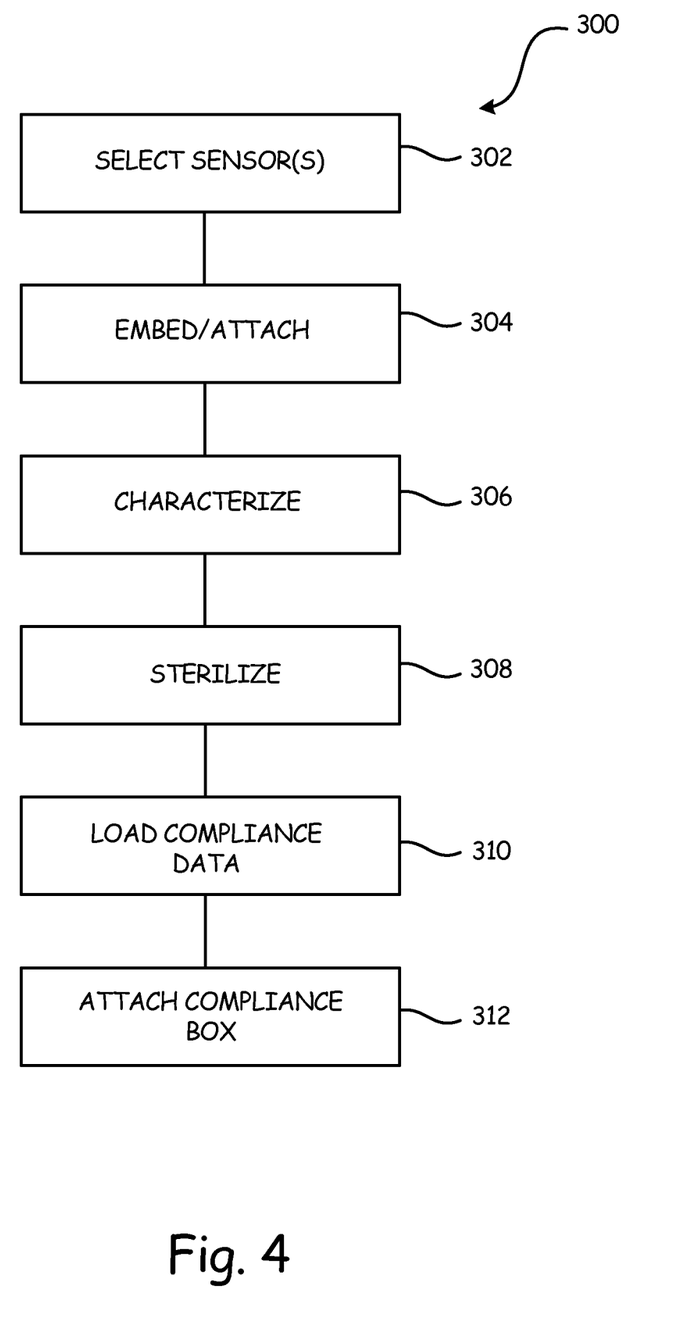
FIG. 4 is a flow diagram of a method of manufacturing a single-use bioreaction bag/sensor assembly in accordance with an embodiment of the present invention.

FIG. 4 is a flow diagram of a method of manufacturing a single-use bioreaction sensing assembly in accordance with an embodiment of the present invention. Method 300 begins at block 302 where one or more sensors are selected for inclusion into the assembly. As set forth above, various types of sensors and/or even sensors of the same type with different performance characteristics can be selected for inclusion in the array. Next, at block 304, the various sensors may be embedded or otherwise attached to a bioreaction bag. However, it is contemplated that the assembly can also be completed, characterized, and loaded with data prior to embedding or attaching to a bag. In such case, the compensated sensor array may simply be provided to a bioreaction bag manufacturer for further manufacturing steps. At block 306, the array of sensors selected at block 302 is characterized. For example, for an array with pH, dissolved oxygen (DO), temperature (T) and pressure (P) sensor, the array would need to be immersed in a buffer solution, such as deionized water, of known pH and dissolved oxygen values. The buffer solution would then be heated and cooled according to sensor requirements. The pH, dissolved oxygen, temperature, and pressure would be monitored throughout the compensation run by reference instruments having a calibration to known standards, such as NIST-traceable standards. The sensor array would be checked, or otherwise monitored at various points against the various references. The number of reference points required for an individual assembly characterization would vary depending on the performance required. In this way, a data set is generated that can be used to compensate the individual sensors of the array.

At block 308, in the embodiment where the array is embedded within a bioreaction bag, the entire bag/sensor assembly may be sterilized. Sterilization is an important requirement of any bioreactor. In the case of conventional stainless steel facilities, this is typically done using a steam CIP process. In the case of a bioreactor poly bag, this is accomplished using heat and a radiation process. In many instances, the radiation process can cause the sensors to shift slightly. If the shift can be measured and predicted, such as by using experimental techniques, then the shift can be compensated by storing compensation information in local storage device 134. At block 310, compliance data, such as characterization data obtained at block 306, shift data, and any other suitable data is loaded into and stored within data storage device 134. Finally, at block 312, the compliance box is attached to the sensor assembly. While FIG. 4 illustrates the compliance box being coupled to the sensor assembly after data is loaded into the compliance box, such coupling can also occur before data is loaded into the compliance box.

Figure 5:
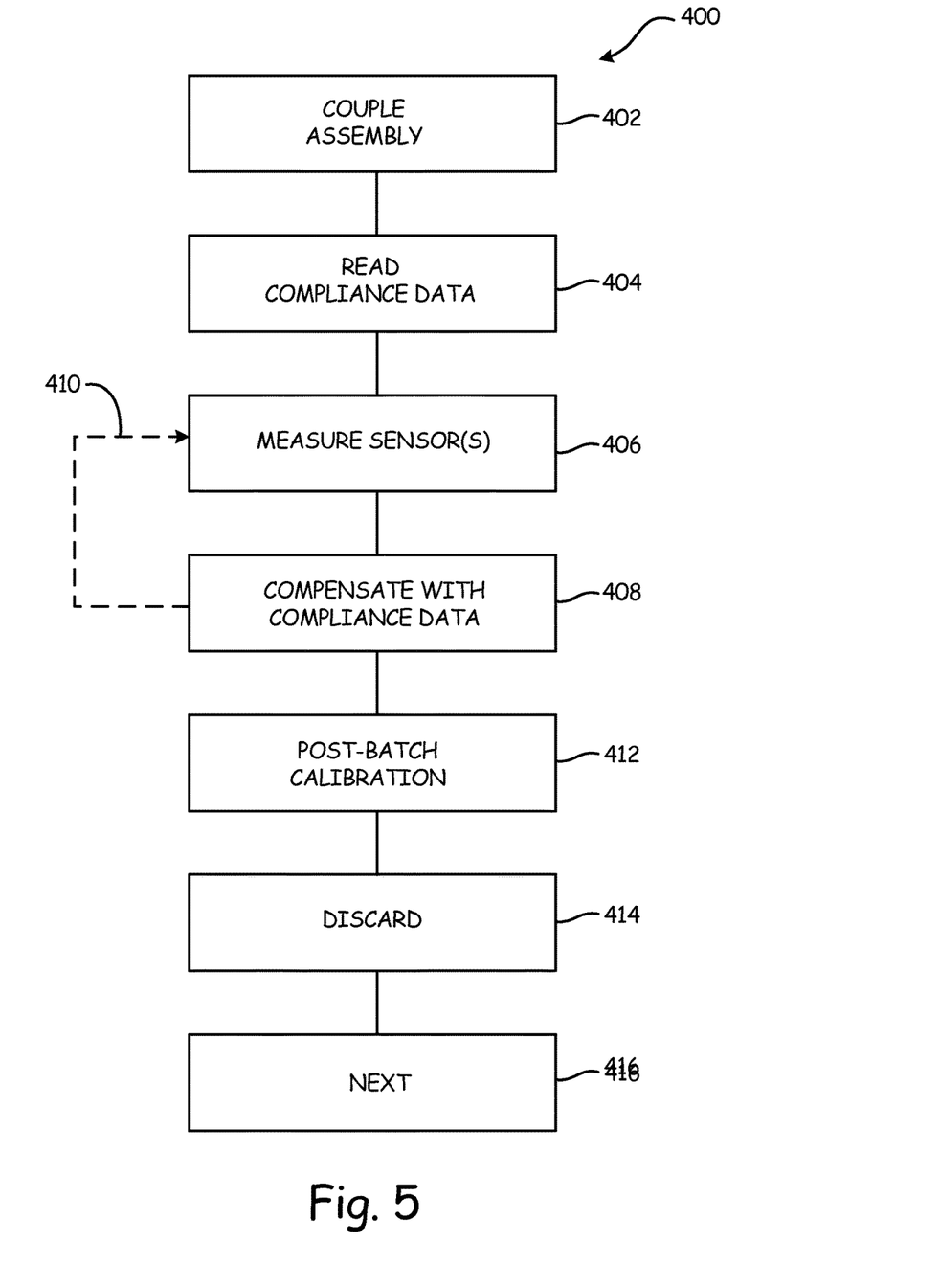
FIG. 5 is a flow diagram of a method of monitoring a bioreaction using a single-use bioreaction sensing system in accordance with an embodiment of the present invention.

FIG. 5 is a flow diagram of a method of operating a single-use bioreaction sensing assembly in accordance with an embodiment of the present invention. Method 400 begins at block 402 where the sensor assembly is coupled to a process variable transmitter. This occurs when connectors 120 and 122 are coupled together. Once so coupled, method 400 continues at block 404 where compliance data is read from the compliance box 116 of the sensor assembly by the transmitter. This step may occur automatically upon detection of the coupling between connectors 120 and 122, or manually in response to an operator input on a local user interface of process variable transmitter 118 or via communication received by process variable transmitter 118 through process communication loop or segment 140. Once the compliance data is received, method 400 continues at block 406 where the individual analog sensor signals are measured by measurement circuitry of process variable transmitter 118. These individual sensor signals are then compensated with the compliance data read at block 404, as illustrated at block 408. Additionally, if the compliance box of the sensor assembly includes any local sensors, such as an absolute pressure sensor, such compliance box sensors can be measured as well. The steps of measuring raw sensor signals and compensating said signals with the compliance data may repeat during the entire bioreaction, as illustrated at dashed line 410. Once the bioreaction is complete, optional block 412 may be performed where post-batch calibration is provided. This post-batch calibration can be performed at the end of the bioreaction/batch run in order to ensure that the instrument was operating correctly and within its designated operating range during the bioreaction. The post-batch calibration information can then be stored by process variable transmitter 118 and/or communicated to control system 124 via process communication loop 140, as desired. Next, at block 414, the bioreaction bag and its contents, as well as the sensor assembly, compliance box and connector 120 are discarded. At block 416, the system is ready to receive the next single-use bioreactor bag/sensor assembly. Once such sensor assembly is coupled to transmitter 118, method 400 repeats.

Although the present invention has been described with reference to preferred embodiments, workers skilled in the art will recognize that changes may be made in form and detail without departing from the spirit and scope of the invention. For example, while embodiments of the present invention have generally been described with respect to a process variable transmitter coupling to the sensor assembly, any device having suitable measurement circuitry and processing capabilities can be used in accordance with embodiments described herein. Additionally, while the description provided above generally includes transmitting the process variable to a control system, embodiments can be practiced where the process variable are simple displayed locally at the measurement device.

What is claimed is:

1. A sensor assembly for a bioreaction container comprising:
   a sensor configured to physically couple to the bioreaction container and sense a first process variable;
   a first absolute pressure sensor configured to physically couple to the bioreaction container and sense a pressure of a sample within the bioreaction container;
   an enclosure operably coupled to the sensor and, the first absolute pressure sensor via leads, the enclosure containing:
      memory that stores compensation data for the sensor and the first absolute pressure sensor; and
      a second, absolute pressure sensor configured to sense a reference pressure within the enclosure to serve as a reference for the sensed pressure of the sample within the bioreaction container;
   a connector physically coupled to the enclosure;
   wherein the sensor and first absolute pressure sensors are configured to undergo sterilization when coupled to the bioreaction container; and
   the memory storing shift data for the sensor and the first absolute pressure sensor, the shift data characterizing how the sensor and the first absolute pressure sensor will be affected by sterilization.

2. The sensor assembly of claim 1, wherein the connector is couplable to a process variable transmitter to allow the process variable transmitter to measure an analog sensor signal of the sensor and the first absolute pressure sensor.

3. The sensor assembly of claim 2, wherein the compensation data is readable by the process variable transmitter to relate each analog sensor signal to a compensated process variable output.

4. The sensor assembly of claim 1, wherein the sensor is of a type selected from the group consisting of pressure sensors, temperature sensors, pH sensors, dissolved oxygen sensors, carbon dioxide sensors, conductivity sensors, and colorimetric sensors.

5. The sensor assembly of claim 4, and further comprising a second sensor selected from the group consisting of pressure sensors, temperature sensors, pH sensors, dissolved oxygen sensors, carbon dioxide sensors, conductivity sensor, and colorimetric sensors, but having a type different than the sensor, and wherein the memory contains compensation data for the second sensor.

6. The sensor assembly of claim 1, wherein the enclosure includes signal conditioning circuitry operably coupled to the sensor and the first absolute pressure sensor.

7. The sensor assembly of claim 6, wherein the signal conditioning circuitry includes at least one preamplifier.

8. The sensor assembly of claim 7, wherein the signal conditioning circuitry includes a preamplifier for the sensor and the first absolute pressure sensor.

9. The sensor assembly of claim 1, wherein the memory stores additional data.

10. The sensor assembly of claim 9, wherein the additional data includes information required by a regulatory body comprising data selected from the group consisting of material construction data, manufacturing date data, serial number data, operating range data and signal type data.

11. The sensor assembly of claim 1, wherein the memory is embodied within a radio-frequency identification (RFID) tag.

12. A bioreaction sensing assembly comprising:
   a single-use bioreaction container;
   a first sensor coupled to the single-use bioreaction container and configured to sense a first condition inside the single-use bioreaction container;
   a second sensor coupled to the single-use bioreaction container and configured to sense a second condition inside the single-use bioreaction container;
   an enclosure operably coupled to each of the first and second sensors, the enclosure containing:
      memory storing shift data characterizing how each of the first and the second sensors will be affected by sterilization; and
   wherein the first and second sensors are configured to be sterilized when coupled to the single-use bioreaction container.

13. The bioreaction sensing assembly of claim 12, and further comprising a connector coupled to the enclosure configured to couple to a process variable transmitter.

14. The bioreaction sensing assembly of claim 13, and further comprising a process variable transmitter configured to couple to the connector and measure a first analog signal relative to the first sensor and calculate a first process variable based on the first analog signal and the compensation data, the process variable transmitter being configured to measure a second analog signal relative to the second sensor and calculate a second process variable based on the second analog signal and the compensation data.

15. The bioreaction sensing system of claim 14, wherein the process variable transmitter is configured to read the compensation data from the memory of the enclosure.

16. The bioreaction sensing system of claim 15, wherein the process variable transmitter includes process communication circuitry configured to communicate in accordance with a process communication protocol.

17. The bioreaction sensing system of claim 16, wherein the process variable transmitter is configured to communicate the first and second process variables using the process communication circuitry.

* * * * *